(12) United States Patent
Finkielsztein et al.

(10) Patent No.: US 8,834,516 B2
(45) Date of Patent: Sep. 16, 2014

(54) METHODS AND APPARATUS FOR A MANUAL VASCULAR COMPRESSION DEVICE

(75) Inventors: Sergio Finkielsztein, Newton, MA (US); Marco Finkielsztein, Newton, MA (US); John N. Vournakis, Charleston, SC (US)

(73) Assignee: Marine Polymer Technologies, Danvers, MA (US)

( * ) Notice: Subject to any disclaimer, the term of this patent is extended or adjusted under 35 U.S.C. 154(b) by 1012 days.

(21) Appl. No.: 11/392,200

(22) Filed: Mar. 29, 2006

(65) Prior Publication Data

US 2006/0229664 A1 Oct. 12, 2006

Related U.S. Application Data

(63) Continuation-in-part of application No. 11/092,369, filed on Mar. 29, 2005.

(51) Int. Cl.
*A61B 17/00* (2006.01)
*A61B 17/12* (2006.01)

(52) U.S. Cl.
CPC ....... *A61B 17/12* (2013.01); *A61B 2017/12004* (2013.01)
USPC ..................................... 606/201

(58) Field of Classification Search
USPC ............... 606/215, 201–204.55; 128/898
See application file for complete search history.

(56) References Cited

U.S. PATENT DOCUMENTS

| | | |
|---|---|---|
| 575,103 A | 1/1897 | Burton |
| 3,228,392 A | 1/1966 | Speyer |
| 3,411,505 A | 11/1968 | Nobis |
| 3,884,240 A | 5/1975 | Gilman |
| 4,572,182 A | 2/1986 | Royse |
| 5,010,902 A | 4/1991 | Rambo et al. |

(Continued)

FOREIGN PATENT DOCUMENTS

| | | |
|---|---|---|
| AT | 295027 B | 12/1971 |
| GB | 12486 A | 0/1910 |

OTHER PUBLICATIONS

Examination Report from related Australian Application No. 2006230231 dated Oct. 25, 2010.

(Continued)

*Primary Examiner* — Melanie Tyson
(74) *Attorney, Agent, or Firm* — Nutter McClennen & Fish LLP

(57) ABSTRACT

A vascular compression apparatus and method for applying pressure onto an area of a patient generally including a blood vessel and a wound site, such as a blood vessel puncture, after a cannulated procedure for the purpose of controlling bleeding and achieving hemostasis. The vascular compression apparatus includes a handle, a shaft and a pad. The shaft extends generally downward from the center of the bottom side of the handle. The pad is connected generally off-center of its top side to the bottom end of the shaft. The bottom side of the pad is convex to allow the vascular compression device to be rocked back and forth. In use, the pad is generally placed proximal to the catheter insertion site and over the blood vessel containing the catheter. The device is rocked proximally to control blood flow while removing the catheter. After the catheter is removed from the puncture site, the device is rocked distally to the puncture site, where pressure is applied until hemostasis is achieved.

4 Claims, 4 Drawing Sheets

(56) References Cited

U.S. PATENT DOCUMENTS

| | | |
|---|---|---|
| 5,133,734 A | 7/1992 | Lee |
| 5,263,965 A | 11/1993 | Roth |
| 5,342,388 A | 8/1994 | Toller |
| 5,554,168 A | 9/1996 | Petersen |
| D387,174 S * | 12/1997 | Gladieux, Jr. ............... D24/214 |
| 5,762,173 A | 6/1998 | Nishimura |
| 5,792,173 A | 8/1998 | Breen et al. |
| 5,873,890 A | 2/1999 | Porat |
| 5,997,564 A | 12/1999 | Schehata et al. |
| 6,004,343 A | 12/1999 | Kurth |
| D475,141 S | 5/2003 | Shin |
| 2003/0028214 A1 * | 2/2003 | Benz et al. .................... 606/201 |
| 2003/0114881 A1 | 6/2003 | Stalemark et al. |
| 2004/0176796 A1 * | 9/2004 | Akerfeldt et al. ............ 606/201 |
| 2006/0095073 A1 * | 5/2006 | Beto et al. .................... 606/201 |
| 2006/0229664 A1 | 10/2006 | Finkielsztein et al. |

OTHER PUBLICATIONS

Extended European Search Report for Application No. 06739894.1 issued Jul. 8, 2013 (7 pages).

* cited by examiner

METHODS AND APPARATUS FOR A MANUAL VASCULAR COMPRESSION DEVICE

CROSS REFERENCE TO RELATED APPLICATIONS

The present application claims the benefit of a U.S. application entitled "Methods and Apparatus for a Manual Vascular Compression Device," bearing Ser. No. 11/092,369, filed Mar. 29, 2005, the entire contents of which are hereby incorporated herein by reference.

FIELD OF THE INVENTION

This invention relates in general to a manual vascular compression device and in particular to a manual femoral compression device.

BACKGROUND OF THE INVENTION

This invention relates to a vascular compression apparatus and method for controlling bleeding and achieving hemostasis by applying pressure onto an area of a patient including a wound site, such as a blood vessel puncture, and a blood vessel. In particular, this invention relates to a vascular compression device and a method for controlling bleeding and facilitating hemostasis following percutaneous catheterization via the femoral artery or vein.

The femoral artery is a high pressure blood vessel which generally requires direct pressure to achieve hemostasis (cessation of bleeding) following completion of a catheterization or cannulation procedure. If, for example, a sheath is removed from the femoral artery in the groin and no attempt to stem the bleeding is made, the patient would quickly experience severe bleeding which would resort in significant consequences including hypovolemia, shock, and possibly death. Hemostasis can often be achieved by applying pressure directly over the femoral artery as well as proximal and medial to the femoral artery puncture site, where such pressure slows or completely occludes blood flow in the artery. This permits a clot to form which causes hemostasis at the puncture site.

Traditionally, to achieve sufficient pressure, an individual must actively press down directly over the artery and proximal and medial to the puncture site for a period of time which varies based on the type of procedure, the nature of the drugs administered and the patient's condition—often for 30 minutes or longer. This can result in fatigue, stiffness and/or pain in the fingers, hands, wrist and forearms of the individual performing the procedure. Prolonged or repeated performance of this procedure may result in a repetitive stress injury such as carpal tunnel syndrome. The direct pressure method also puts the individual administering pressure at risk for direct exposure to the patient's blood.

Various types of automated manual solutions have been developed to, in part, address these issues. One example of an automated solution is shown by Petersen in U.S. Pat. No. 5,554,168. Petersen describes a free standing apparatus which may be attached to the bottom frame of a hospital bed. A pressure applying head is mounted on a swing arm attached to the vertical shaft of the base and can be positioned directly above the wound. Pressure is developed by either compressed air or an electric motor. Two pressure shoes can be positioned to provide both vertical and horizontal pressure.

Another automated solution is described by Lee in U.S. Pat. No. 5,133,734. Lee discloses a pneumatically operated femoral artery compressor applying calibrated and calibrateable external pressure on the puncture site of the femoral artery with the plunger end of a mounted pressurized assembly.

Breen et. al describe another type of partly automated solution, which also uses pneumatic pressure, in U.S. Pat. No. 5,762,173. Breen describes a wound closure device that includes an inflatable balloon with an inflation and deflation outlet. The balloon is coupled to patch, having an aperture for receiving the inflation/deflation outlet. The assembly is coupled to the placement patch and is held via a belt strap at either the wound site or on a bleeding vessel.

These automated compression devices are far from ideal, however. They tend to be expensive, difficult to maintain in good working order, consume a great deal of space and are difficult to keep sterile.

A number of manual compression devices have been described as well. Roth, in U.S. Pat. No. 5,263,965, describes a device that is used to apply direct pressure to arterial and venous incisions to promote hemostasis. It consists of a round flat disk with a user manipulable member used for applying downward pressure. In the preferred embodiment of the invention, the user manipulable member consists of a peg over which a cylindrical weight is pivotally mounted. A stretchable bandage is used to secure the weight in place.

Another type of manual compression device is described by Toller in U.S. Pat. No. 5,342,388. This manual compression aid is comprised of a cylindrically shaped handle above a sterile disposable disk. The disk is placed above the catheter insertion point with the catheter inside the notch of the disk. As the catheter is removed, pressure is applied to the handle to force the disk to compress the artery and thereby control bleeding—ultimately achieving hemostasis. This type of device has a number of disadvantages including: the cost of the apparatus; the difficulty associated in ensuring a minimal level of cleanliness; and the time associated in connecting the disposable disk to the assembly prior to its use on a patient.

Benz et. al describe another form of manual compression device in Pub No. US 2003/0028214. This manual vascular compression device also includes a handle an elongated shaft and a pad or disk. In this device the pad or disk is integral to the assembly and the entire apparatus is disposable. Like the pad of Toller, the pad is flat and contains a notched or equivalent area for locating the catheter.

All these devices, however, provide for straight vertical compression at a single location. This type of compression provides for suboptimal control of the artery or vein ultimately extending the time for achieving hemostasis.

SUMMARY OF THE INVENTION

The invention provides for an improved manual apparatus for assisting a user in controlling bleeding and achieving hemostasis. The invention more particularly provides for a manual vascular compression device.

An object of the invention is to assist a user in controlling bleeding and achieving hemostasis with a hand held device that allows for compression of a puncture site at both the skin level and blood vessel level simultaneously.

A further object of the invention is to assist a user in controlling bleeding and achieving hemostasis after removing a catheter or cannula from a blood vessel by providing for compression along the angle of the catheter or cannula track from the skin, to the blood vessel, rather than traditional straight vertical compression.

A further object of the invention is to provide for a manual femoral compression device that facilitates hemostasis following percutaneous catheterization via the femoral artery or vein.

These and other objects are achieved with the vascular compression apparatus described herein. The vascular compression apparatus is comprised of a handle, a shaft, and a pad. The proximal end of said shaft connects to said handle generally off-center of the bottom side of the handle. Said pad connects to the distal end of the shaft generally in the center of the top side of the pad. The bottom-side of the pad is slightly convex or curved in a manner that allows the user to rock the device proximally, for proximal control of blood flow while retrieving a device such as a catheter from a puncture site, followed by distal rocking of the device to the puncture site to achieve hemostasis. By providing varying degrees of pressure the user can alternatively compress the puncture site at the skin level and at the blood vessel level as well.

The pad, unlike a number of the prior art pads, contains no notch to enable proper placement of the of the vascular compression apparatus onto the body surface in proximity to a puncture site. In a preferred embodiment of the invention, the vascular compression device is made of a transparent or translucent material and a visual guide is provided, which overlies the blood vessel for which compression is desired, and follows the path of the blood vessel. In addition, the transparent or translucent material permits visualization of, and access to, the puncture site while compression is being applied. In a most preferred embodiment a grooved guide is provided to allow alignment of the catheter.

Additionally, because the pad is slightly elongated and the handle is off-center, the user can optionally place their other hand on either the top side of the pad or on the handle of the device to help stabilize the device and provide for additional pressure if necessary.

In one embodiment, the handle and elongate shaft of the vascular compression apparatus are formed as a single member and the pad is removably connected to the elongate shaft. In a preferred embodiment the pad is a unitary piece. In another preferred embodiment the pad is comprised of two or more components each of which is removably connected to either the elongated shaft or to another component of the pad.

In another preferred embodiment, the vascular compression apparatus is formed as a unitary member with the pad permanently connected to the elongate shaft, thereby requiring no assembly or disassembly by the user and which further allows for easy and complete sterilization. In a most preferred embodiment the unitary vascular compression apparatus is disposable.

Optionally the invention may be used with an external vascular closure device. Traditionally a simple gauze pad or bandage can be used with the invention to aid in hemostasis. The bandages may come in various forms and include a standard gauze pad, a U.S. Army First Aid Field Bandage or other types of bandages. Recently new types of externally applied vascular closure devices have been developed that further decrease the time to hemostasis following catheterization. These include products that are based on a variety of macromolecules such as collagen, cellulose, chitosan and Poly-N-Acetyl Glucosamine (PGlcNAc). Commercially available products include: Actifoam™ (C.R. Bard, Inc. Murray Hill, N.J.), a collagen sponge; Surgicel (J&J Medical, Arlington, Tex.), a cellulose based product; Clo-Sur PAD™ (Scion Cardio-Vascular, Miami, Fla.), and Chito-Seal (Abbot Laboratories, Abbot Park, Ill.), both chitosan based products; and SyvekPatch® a pGLcNAc based product. Most preferably, the device is used with a SyvekPatch®.

Furthermore, the invention contemplates a kit comprising the manual femoral compression apparatus and an external vascular closure device. The kit is preferably sterile. In a most preferred embodiment one or more of the components of the kit are disposable.

DETAILED DESCRIPTION OF THE INVENTION

Figure 1:
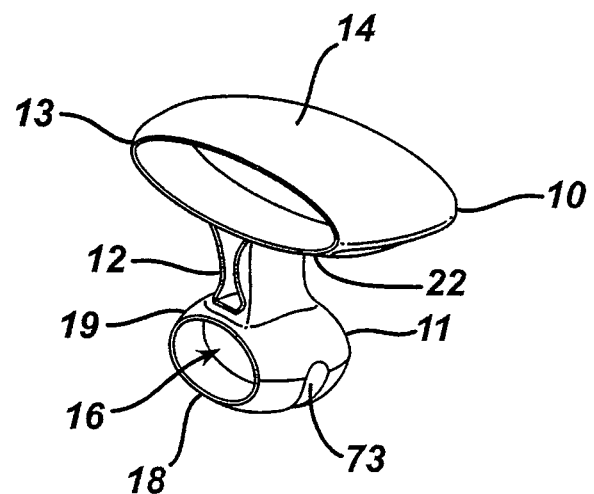
FIG. 1 is a perspective view of the invention.

To more clearly set forth the invention, reference will be made to the embodiments illustrated in the drawings and specific language will be used. Nevertheless, it should be understood that the invention should not be deemed limited to particular embodiments, descriptions or drawings contained herein.

The vascular compression apparatus of the invention is used on a patient to apply pressure on an area near or at a wound site, such as a blood vessel puncture, most often after a cannulated procedure such as angioplasty, for the purpose of controlling the patient's bleeding and, further, of achieving hemostasis.

FIG. 1 shows the manual vascular compression device of the invention 10. The device has a handle 13 having a top 14 and a bottom 22, a shaft 12 and a pad 11. The handle 13 is connected, generally off-center, to the proximal end of the shaft 12. The pad 11 is connected to the distal end of the shaft 12 and is generally centered on the top surface 19 of the pad 11. The handle 13 is generally elongated and may include solid or, as pictured, substantially hollow sides. The bottom 18 of the pad 11 is generally convex to allow for rocking of the device. In a preferred embodiment, the top 19 of the pad 11 is also convex.

FIG. 1 further shows the handle 13 as generally elongated. In a preferred embodiment the bottom 22 of the handle is slightly convex. When downward pressure is applied by a user on the handle 13, such pressure is transferred through the shaft 12 to the pad 1/. The pad 11 depresses the area of the body surface upon which it rests, thereby compressing either the lumen of the blood vessel over which it is placed to partially or completely occlude the blood vessel or directly on a blood vessel puncture site to achieve hemostasis. In a preferred method of the invention, the user places the device over the puncture site and rocks the device 10 proximal to the puncture site and applies pressure for proximal control of blood flow while retrieving a medical device, such as a catheter, from the site. The user then distally rocks the device to the puncture site and applies pressure to achieve hemostasis.

Figure 2:
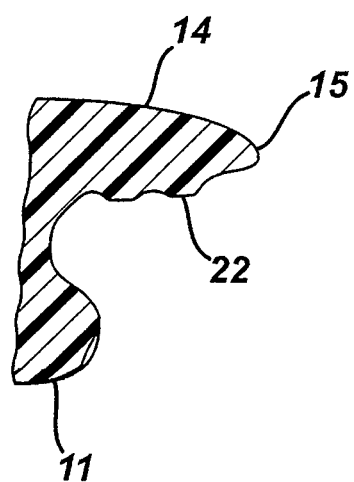
FIG. 2 is a side sectioned view of the invention shown in FIG. 1.

FIG. 2 shows a side sectioned view of the invention.

Figure 3:
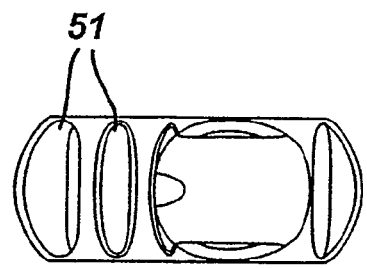
FIG. 3 is a top view of the invention.

FIG. 3 shows a bottom view of the device 10.

Figure 4:
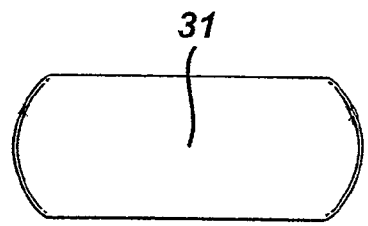
FIG. 4 is a bottom view of the pad of the invention.

FIG. 4 shows a top view 14 of the handle 13. A vessel alignment guide 31 is provided to help the user align the device with the blood vessel and ultimately provide for compression following the angle of a catheter track. Visual guides may also provided to indicate the location of the patient's feet or head relative to the device.

Figure 5:
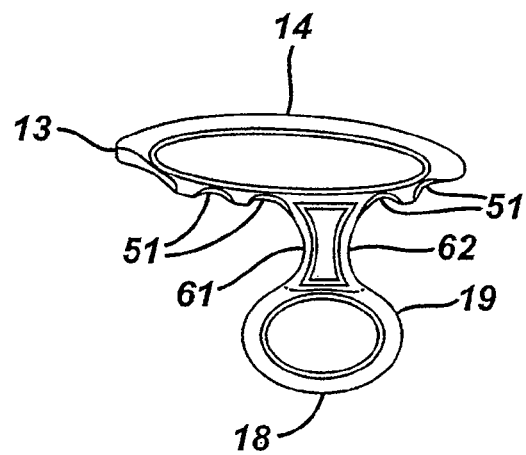
FIG. 5 is a side view of the invention.

FIG. 5 shows a side view of the vascular compression apparatus 10. This illustrates more clearly the convex nature of the pad 11 bottom 18. A series of optional grooves 51 are shown on the bottom side 22 of the handle 13. These grooves allow the user to place their fingers on the bottom side 22 of the handle 13 to either assist in rocking the device or aid in applying additional downward pressure on the pad in a manner that provides for additional stability of the device. The shaft 12 has a distal or front side 61 and a proximal or rear side 62. In a preferred embodiment, sides 61 and 62 are concave.

Figure 6:
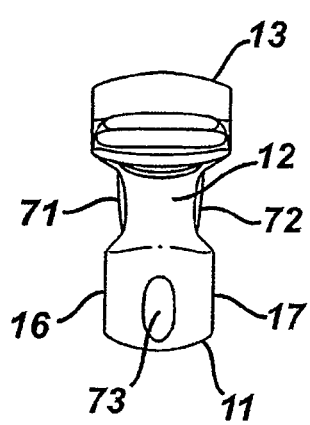
FIG. 6 is a front view of the invention.

FIG. 6 shows a front view of the vascular compression apparatus 10. The front of the device is oriented so that it is oriented distally and faces the patient's feet. The pad 11 contains a groove 73 which can be used to help guide the removal of the catheter. The groove is oriented approximately medially to the pad and generally distally. Sides 71 and 72 of the handle may be solid or as pictured substantially hollow to save on weight. In addition, the pad 11 has sides 16 and 17, which may be solid or, as pictured, substantially hollow.

The vascular compression device is generally molded of a mostly rigid material, for example, an acrylic or a plastic. The only requirement is that the material is sturdy enough to withstand the application of downward pressure onto a human patient, sufficient to cause a complete occlusion of an artery. The vascular compression apparatus 10 may be packaged and sterilized as a sterile medical product so that the user need not clean or wash it prior to its use. In a preferred embodiment the material is transparent so that the user can more easily align the device with the wound, the relevant artery or vein and/or the catheter or cannula being removed.

The pad 11, in a preferred embodiment, when viewed from the side is shaped as an oval knob, preferably having open or recessed sides and a generally constant dimension between the side surfaces of the pad 11.

The handle 13 is generally somewhat elongated. This shape enables a user to place the base of the palm of their hand directly over the topmost area of the handle 13 and, bending their wrist so that the palm of their hand faces downward. By keeping their elbow straight, they can comfortably apply pressure downwards without significant exertion of muscles in the forearm, wrist or hand while maintaining a relatively stable attitude of the vascular compression apparatus 10.

The proximal end of the shaft 12 connects to the handle 11 generally off-center of the bottom 22 of the handle 13. In a preferred embodiment, the shaft 12 may have a front 61 and back 62 that are convex. The sides 71 and 72 of the shaft 12 can be either solid or partially hollow to reduce the weight of the device. The length of the shaft 12 is at least sufficient to provide ample space for motion of the user's fingers when using the vascular compression apparatus 10 on a patient, but not so long that it inhibits the user's ability to maintain a generally straight elbow and stable attitude in the application of downward pressure.

In prior art devices the pad is generally placed proximal to the catheter insertion site and over the blood vessel containing the catheter. The catheter or cannula is then removed from the blood vessel and pressure applied to the handle by the user in a downward direction to force the pad to compress the blood vessel for the purpose of controlling bleeding and, farther, to achieve hemostasis.

In the device of the invention, the convex pad bottom 18 as well as the off-center placement of the shaft 12, relative to the attached handle 13 permit easy rocking of the device both proximally and distally from the puncture or wound site allowing for control of blood flow both before and after removal of a catheter, or similar device. Specifically, a user would place the device 10 over a catheter insertion site and parallel to the blood vessel containing the catheter preferably by positioning the device using the visual guides indicating the location of the patient's feet and head and aligning the device using the vessel alignment guide 31. The user would then apply downward pressure from the shoulders onto the handle 13 and through the shaft 12 while rocking the device 10 proximally along the blood vessel. The user would then retrieve the catheter or cannula from the puncture site. The user would then rock the device 10 distally towards and optionally over the puncture site while still exerting sufficient downward pressure to achieve hemostasis.

In another alternative embodiment, the handle 13 and shaft 12 of the vascular compression apparatus 10 may be formed as a single member, to which the pad 11 may be removably connected by the user prior to use. In a further alternative embodiment the removeable pad is disposable. Methods for attaching disposable pads to vascular compression devices are well known in the art and have been described by Toller in U.S. Pat. No. 5,342,388 and Royce in U.S. Pat. No. 4,572,182, which disclosures are hereby incorporated by reference.

The invention further contemplates a pad 11 for a vascular compression device 10 that is substantially convex. In particular, a pad for a manual vascular compression device that is convex is contemplated.

In another alternative embodiment, certain portions of the vascular compression apparatus may be treated or have applied to it a material to modify the coefficient of friction of the surfaces to which such treatment or material is applied. An application of this treatment or material has the effect of minimizing or eliminating slippage so that post-catheterization complications at the puncture site are avoided, where such treatment or material is applied to the bottom surface 18 of the pad 11. Such treatment or material may also prevent slippage of the vascular compression apparatus in the user's hand, also helping to prevent slippage or other undesired movement on the patient's body surface, where such treatment or material is applied to the top surface of the handle 13.

In another alternative embodiment, certain portions of the bottom 22 of the handle 13 of the vascular compression apparatus 10 may be modified to contain grooves 51 for the optional placement of the user's fingers. The ability for the user to place their fingers directly on the pad, further minimizes or eliminates the possibility of slippage, and provides for better control of the device so that post-catheterization complications at the puncture site are avoided.

In another alternative embodiment, the composition of the vascular compression apparatus 10 may be changed to a heavier material, or material may be added to portions of the vascular compression apparatus to make it sufficiently heavy to achieve partial or total occlusion of a blood vessel with little or no exertion of downward pressure on the handle 13.

Figure 7:
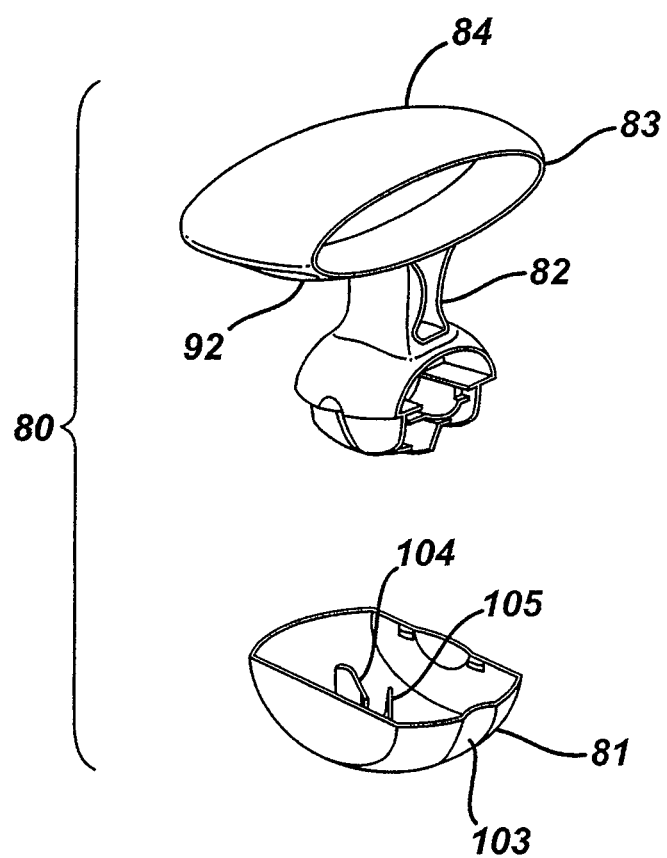
FIG. 7 is an expanded perspective view of an alternative embodiment of the invention.

FIG. 7 shows a further embodiment of the manual vascular compression device of the invention. The device 80, of the embodiment of FIG. 7 has a handle 83 having a top 84 and a bottom 92, a shaft 82 and a removable pad 81. The handle 83 is connected, generally off-center, to the proximal end of the shaft 82. The pad 81 is removeably connected to the distal end of the shaft 82 and is generally centered on the pad 81. The pad 81 contains a groove 103 which can be used to help guide the removal of the catheter. The groove is oriented approximately medially to the pad and generally distally. Guides 104 and 105 are optionally provided to aid in proper orientation of the pad 81. Pad 81 may be connected to the handle 83 in any number of ways including friction or pressure fit, through the use of clips, negative pressure (suction) or other ways. Pad 81 is generally disposable while the handle 83 of the instant embodiment is generally reusable. The pad 81 and handle 83 are preferably made of biocompatible plastics suitable for sterilization. In one aspect of the invention, the handle is made of Plexiglas® and the removable component is made of a polypropylene random co-polymer.

Figure 8:
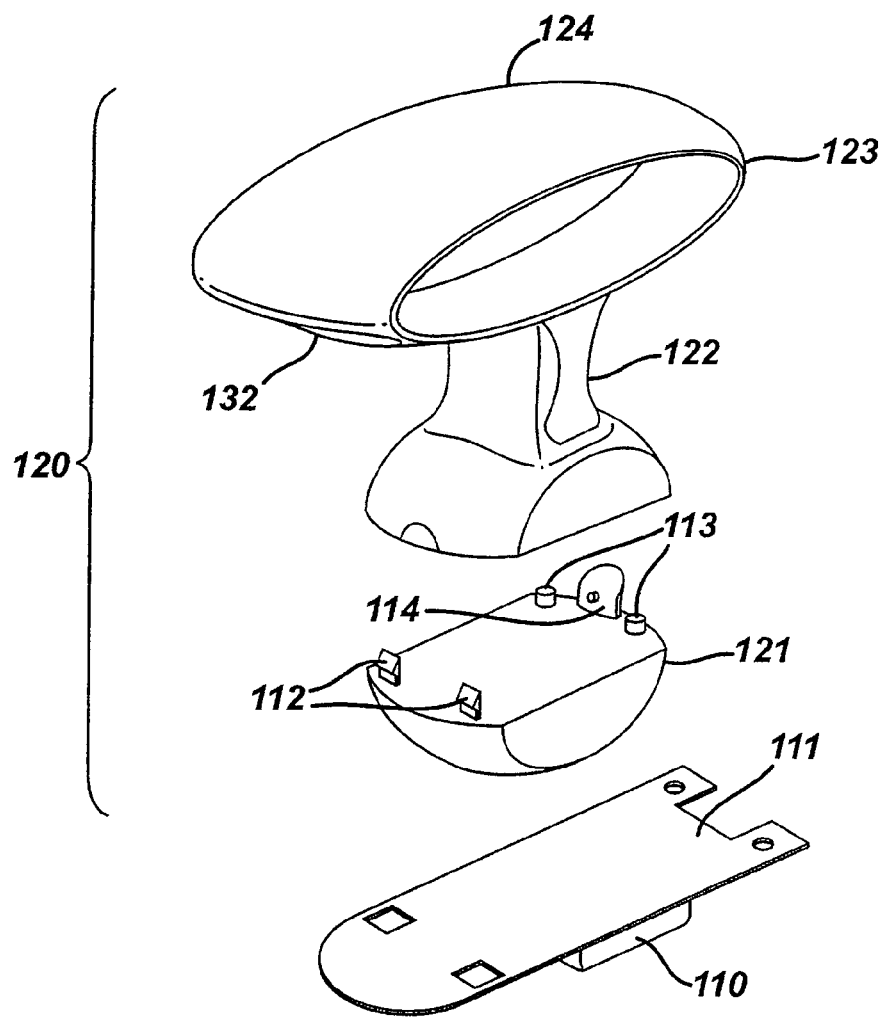
FIG. 8 is an expanded perspective view of a further embodiment of the invention.

FIG. 8 shows another further embodiment of the invention. Like in FIG. 7, the device 120, of the embodiment of FIG. 8 has a handle 123 having a top 124 and a bottom 132, a shaft 122 and a removable pad 121. The handle 123 is connected, generally off-center, to the proximal end of the shaft 122. The pad 121 is removeably connected to the distal end of the shaft 122 and is generally centered on the pad 121. The pad 121 optionally includes a groove that can be used to help guide the removal of the catheter. In the instant embodiment, the device 120 may be used with an external vascular closure device 110 such as a gauze pad or bandage, as described previously. The pad 110 may be attached to a support 111 for securing to the pad 121. The support 111 attaches to the pad 121 through a series of clips 112 and pegs 113. The pad 121 may be attached to the shaft 122 using any number methods including an internal clip 114.

Kits of the invention are also contemplated comprising one or more of the following components: the vascular compression device of the invention (either a unitary reusable vascular compression device or a device with a reusable handle and a disposable pad); an external vascular closure device such as a gauze pad or bandage; and an adhesive bandage. In a preferred embodiment of the kits of the invention, the external vascular closure device is made of Poly-N-Acetyl Glucosamine and the bandage is a transparent adhesive bandage.

This detailed description of the invention is for illustrative purposes only. A reading by those skilled in the art will bring to mind various changes without departing from the spirit and scope of the invention.

What is claimed is:

1. A method for facilitating hemostasis at a wound site, following percutaneous catheterization of a vessel using a manual vascular compression device, where a catheter has been inserted in the wound site, wherein the manual vascular compression device comprises a handle, a shaft extending generally perpendicular from said handle and a convex pad having a top side and a bottom side and connected to said shaft on a top side at a distal end from said handle, wherein the manual vascular compression device is made of mostly rigid material and wherein the handle, the shaft and the pad are made of mostly rigid material and are formed as a single member, comprising the steps of:
 (a) placing the pad of the device at the wound site parallel to a blood vessel;
 (b) manually rocking the pad of the device proximally along the blood vessel and applying pressure to control blood flow;
 (c) removing the catheter; and
 (d) manually rocking the pad of the device distally towards the wound site parallel to the blood vessel and applying pressure until hemostasis occurs;
 wherein said step (b) of manually rocking the pad of the device proximally along the blood vessel and applying pressure to control blood flow is performed while removing the catheter.

2. The method of claim 1 wherein the blood vessel is a femoral artery.

3. The method of claim 1 wherein the blood vessel is a femoral vein.

4. The method of claim 1, wherein said step (d) of manually rocking the pad of the device distally towards the wound site parallel to the blood vessel and applying pressure until hemostasis occurs is performed after the catheter is removed.

* * * * *